United States Patent [19]

Helioff et al.

[11] Patent Number: 5,118,498
[45] Date of Patent: Jun. 2, 1992

[54] HAIR SETTING SHAMPOO COMPOSITION

[75] Inventors: Michael W. Helioff, Westfield; Krystyna Plochocka, Scotch Plains, both of N.J.; Mohammed Tazi, Marietta, Ga.

[73] Assignee: ISP Investments Inc., Wilmington, Del.

[21] Appl. No.: 615,184

[22] Filed: Nov. 19, 1990

[51] Int. Cl.$^5$ .................. A61K 7/06; A61K 7/11; A61K 31/21
[52] U.S. Cl. ..................... 424/70; 424/71; 424/DIG. 2; 514/506
[58] Field of Search ............ 424/71, 70, DIG. 2, 424/78; 252/DIG. 13, 550

[56] References Cited

U.S. PATENT DOCUMENTS

| | | | |
|---|---|---|---|
| 3,819,540 | 6/1974 | Paviak | 252/555 |
| 4,240,450 | 12/1980 | Grollier | 424/71 X |
| 4,402,977 | 9/1983 | Grollier | 424/70 |
| 4,900,809 | 3/1990 | Tazi et al. | 526/271 X |
| 4,962,185 | 10/1990 | Tazi et al. | 528/497 |

FOREIGN PATENT DOCUMENTS 125711 11/1984 European Pat. Off. ........... 252/550

*Primary Examiner*—Thurman K. Page
*Assistant Examiner*—S. Gardner
*Attorney, Agent, or Firm*—Walter Katz; Marilyn J. Maue; Joshua J. Ward

[57] ABSTRACT

The hair setting shampoo composition of the invention comprises a resin provided by about 1–15% by weight of about a 20–50% resin active alcoholic solution of the alkyl half-ester of a $C_1$–$C_5$ alkyl vinyl ether-maleic anhydride copolymer having a molecular weight of at least one million, which is about 5–90% neutralized, preferably with about 0.01–1% by weight of 2-amino-2-methyl-1-propanol, about 5–60% by weight of a surfactant, optionally 0–10% by weight of added ethanol, and about 30–90% by weight of water. The composition provides a subtle temporary set on hair of the user without the use of auxiliary fixatives in the composition.

9 Claims, No Drawings

HAIR SETTING SHAMPOO COMPOSITION

BACKGROUND OF THE INVENTION

1. Field of the Invention

This invention relates to shampoo cosmetic formulations, and more particularly, to a hair setting shampoo composition which provides a subtle, temporary set for the hair of the user.

2. Description of the Prior Art

Current hair setting shampoo formulations generally are comprised of anionic surfactants and resins in combination with auxiliary ingredients designed to improve combability, luster, shine and manageability. However, for men and women with short and curly hair, or short and wavy hair, it is desired to provide a thick, clear setting shampoo which will provide a subtle, temporary set without additional fixatives in the composition. Such a setting shampoo formulation also should prevent frizziness which often occurs after shampooing.

SUMMARY OF THE INVENTION

The hair setting shampoo composition of the invention comprises a resin provided by about 1–15% by weight of about a 20–50% resin active alcoholic solution of the alkyl half-ester of a $C_1$–$C_5$ alkyl vinyl ether-maleic anhydride copolymer having a molecular weight of at least one million, which is about 5–90% neutralized, preferably with about 0.01–1% by weight of 2-amino-2-methyl-1-propanol, about 5–60% by weight of a surfactant, optionally 0–10% by weight of added ethanol, and about 30–90% by weight of water. The composition can contain also preservatives, chelating agents, fragrance etc. The composition provides a subtle temporary set on hair of the user without the use of auxiliary fixatives in the composition.

DETAILED DESCRIPTION OF THE INVENTION

The thick, clear setting shampoo composition of the invention includes the alkyl half-ester of a high molecular weight $C_1$–$C_5$ alkyl vinyl ether-maleic anhydride copolymer. The copolymer with $C_1$-vinyl ether is available commercially in powder form as Gantrez ® AN-169 (GAF Chemicals Corp.), which is a methyl vinyl ether-maleic anhydride copolymer having a molecular weight of about one million, or more. Suitable alkyl half-esters of this copolymer include the ethyl or butyl compounds. Solutions of such Gantrez ® AN-169 half-esters are prepared as about a 20–50% resin active solution in ethanol.

The composition of the hair setting composition is given in Table 1 below.

TABLE 1

HAIR SETTING SHAMPOO COMPOSITION

| Component | Concentration (% by Wt.) | | |
|---|---|---|---|
| | Suitable | Preferred | Optimum |
| A. Gantrez ® AN-169 (Half-Ester Solution) (20–50% Active) | 1–15 | 3–10 | 5 |
| B. Surfactant | 5–60 | 10–40 | 34 |
| C. Resin Neutralizing Agent, e.g. AMP | 0.01–1 | 0.05–0.5 | 0.1 |
| D. Ethanol (95%) | 0–10 | 1–5 | 2.5 |
| E. Water | 30–90 | 40–80 | 58.4 |

A typical setting shampoo formulation is the following:

TABLE 2

| Component | % by Weight |
|---|---|
| Resin | |
| Gantrez ® AN-169 (Ethyl half-ester, 26% active in ethanol, molecular weight of one million or higher) | 5 |
| Surfactant | |
| Ammonium Lauryl Sulfate (100% basis) | 10 |
| Ammonium Laureth Sulfate | 10 |
| Alipal ® HF-433 (Rhone-Poulenc) | 10 |
| Surfadone ® LP-300 (GAF) | 2 |
| Lauric Diethanolamide (100%) | 2 |
| Resin Neutralizing Agent 2-Amino-2-Methyl-1-Propanol | 0.11 |
| Alcohol Ethanol (95%) | 2 |
| Chelating Agent Cheelox ® | 0.2 |
| Preservative Germaben ® | 1 |
| Perfume Fragrance | 0.25 |
| Aqueous Medium Water | 57.7 |
| | 100.0 |

The surfactant component of the composition of the invention suitably is present in an amount of about 5–60% by weight of the composition and may be selected from conventional surfactants known in the art and used in hair shampoo formulations. Typically the major portion of the surfactant is ammonium lauryl sulfate, although mixtures with such commonly used surfactant materials as ammonium laureth sulfate and lauric diethanolamide may be used as well. Other surfactants such as Alipal ® HF-433 (Rhone-Poulenc) and Surfadone ® LP-300 (GAF) may be included, if desired.

The preferred resin neutralizing agent is 2-amino-2-methyl-1-propanol (AMP), although ammonium hydroxide may be used as well.

The added ethanol component is optional and may be included to provide a sufficient amount of alcohol to solubilize the composition. A volatile solubilizer, such as dimethyl ether, also may be used.

Other optional components are conventional and include preservatives, perfumes and chelating agents.

The water phase is provided by deionized water, usually in an amount of about 30–90% by weight.

The composition is prepared by heating the water component to about 70° C., stirring, and then slowly adding the surfactant ingredients over about a 30-minute period. Then the mixture is cooled to 25°–30° C. and the chelating agent is added. Then ethanol, AMP and the resin solution components are admixed in a separate vessel, and the water-surfactant mixture is added thereto. Then the preservative and fragrance is added thereto.

The resulting formulation is a thick, clear hair setting shampoo. In use on short and curly hair, or short and wavy hair, this setting shampoo composition provides a subtle, temporary set with effective combability, luster, shine and manageability. In addition, frizziness is avoided during use.

While the invention has been described with particular reference to certain embodiments thereof, it will be understood that changes and modifications may be made which are within the skill of the art. Accordingly, it is intended to be bound only by the following claims, in which:

What is claimed is:

1. A hair setting shampoo composition comprising a resin provided by about 1–15% by weight of about a 20–50% resin active alcoholic solution of the ethyl or butyl alkyl half-ester of a $C_1$–$C_5$ alkyl vinyl ether-maleic anhydride copolymer having a molecular weight of at least about one million, which is about 5–90% neutralized, about 5–60% by weight of a surfactant, 0–10% by weight of added ethanol, and about 30–90% by weight of water.

2. A composition according to claim 1 wherein said $C_1$–$C_5$ alkyl vinyl ether is the methyl vinyl ether.

3. A composition according to claim 1 wherein said surfactant includes ammonium lauryl sulfate.

4. A composition according to claim 2 wherein said surfactant also includes at least one of ammonium laureth sulfate and lauric diethanolamide.

5. A composition according to claim 1 wherein said resin is neutralized with 2-amino-2-methyl-1-propanol.

6. A composition according to claim 1 comprising about 3–10% by weight of said resin solution, about 10–40% by weight of said surfactant, about 0.05–0.5% by weight of a resin neutralizing agent, 0–5% by weight of added ethanol and about 40–80% by weight of water.

7. A composition according to claim 1 which includes at least one of a chelating agent, a preservative and a fragrance.

8. A composition according to claim 1 comprising about 5% by weight of the resin solution, about 34% by weight of surfactant, about 0.1% by weight of the resin neutralizing agent, about 2.5% by weight of added ethanol and about 58.4% by weight of water.

9. A composition according to claim 7 which includes at least one of a chelating agent, a preservative and a fragrance.

* * * * *